US00PP27808P3

(12) United States Plant Patent
Miyazaki

(10) Patent No.: US PP27,808 P3
(45) Date of Patent: Mar. 21, 2017

(54) ***LOBELIA* PLANT NAMED 'SUNLOBE TOREHO'**

(50) Latin Name: *Lobelia erinus*
Varietal Denomination: Sunlobe Toreho

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 45 days.

(21) Appl. No.: 14/545,748

(22) Filed: Jun. 15, 2015

(65) Prior Publication Data

US 2016/0366807 P1 Dec. 15, 2016

(51) Int. Cl.
*A01H 5/02* (2006.01)

(52) U.S. Cl.
USPC ..... Plt./451

(58) Field of Classification Search
USPC ..... Plt./451
See application file for complete search history.

*Primary Examiner* — Keith Robinson
(74) *Attorney, Agent, or Firm* — C. A. Whealy

(57) ABSTRACT

A new and distinct cultivar of *Lobelia* plant named 'Sunlobe Toreho', characterized by its outwardly spreading plant habit; vigorous growth habit; freely branching habit; dense and bushy plant form; freely flowering habit; relatively large white-colored flowers; and good garden performance.

1 Drawing Sheet

Botanical designation: *Lobelia erinus.*
Cultivar denomination: 'SUNLOBE TOREHO'.

BACKGROUND OF THE INVENTION

The present invention relates to a new and distinct cultivar of *Lobelia* plant, botanically known as *Lobelia erinus* and hereinafter referred to by the name 'Sunlobe Toreho'.

The new *Lobelia* plant is a product of a planned breeding program conducted by the Inventor in Higashiomi, Shiga, Japan. The objective of the breeding program is to create new outwardly spreading, freely-branching and bushy *Lobelia* plants with large attractive flowers and good garden performance.

The new *Lobelia* plant originated from an open-pollination in May, 2007 of a proprietary selection of *Lobelia erinus* identified as code named ANB-LK, not patented, as the female, or seed, parent with an unknown selection of *Lobelia erinus* as the male, or pollen, parent. The new *Lobelia* plant was discovered and selected by the Inventor as a single flowering plant within the progeny of the stated open-pollination in a controlled greenhouse environment in Higashiomi, Shiga, Japan in June, 2008.

Asexual reproduction of the *Lobelia* plant by vegetative cuttings in Higashiomi, Shiga, Japan since April, 2009 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobe Toreho'. These characteristics in combination distinguish 'Sunlobe Toreho' as a new and distinct *Lobelia* plant:

1. Outwardly spreading plant habit.
2. Vigorous growth habit.
3. Freely branching habit; dense and bushy plant form.
4. Freely flowering habit.
5. Relatively large white-colored flowers.
6. Good garden performance.

Plants of the new *Lobelia* differ primarily from plants of the female parent selection in flower color as plants of the female parent selection have sky blue-colored flowers with white-colored centers.

Plants of the new *Lobelia* can be compared to plants of *Lobelia erinus* 'Lobwhi', disclosed in U.S. Plant Pat. No. 25,205. In side-by-side comparisons conducted in Higashiomi, Shiga, Japan, plants of the new *Lobelia* differed from plants of 'Lobwhi' in the following characteristics:

1. Plants of the new *Lobelia* were more outwardly spreading than plants of 'Lobwhi'.
2. Plants of the new *Lobelia* had larger leaves than plants of 'Lobwhi'.
3. Plants of the new *Lobelia* had larger flowers than plants of 'Lobwhi'.
4. Plants of the new *Lobelia* had longer pedicels than plants of 'Lobwhi'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobe Toreho' grown in a container.

The photograph at the bottom of the sheet is a close-up view of a typical flowering plant of 'Sunlobe Toreho'.

DETAILED BOTANICAL DESCRIPTION

Plants used for the aforementioned photographs and following description were grown in 15-cm containers in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Lobelia erinus* 'Sunlobe Toreho'.

Parentage:

*Female, or seed, parent.*—Proprietary selection of *Lobelia erinus* identified as code name ANB-LK, not patented.

*Male, or pollen, parent.*—Unknown selection of *Lobelia erinus*, not patented.

Propagation:

*Type cutting.*—Vegetative cuttings.

*Time to initiate roots, summer and winter.*—About one week at temperatures about 15° C. to 20° C.

*Time to produce a rooted young plant, summer and winter.*—About three weeks at temperatures about 15° C. to 20° C.

*Root description.*—Fibrous.

*Rooting habit.*—Freely branching; relatively dense.

Plant Description:

*Plant and growth habit.*—Outwardly spreading plant habit; freely branching habit with lateral branches developing at potentially every node; dense and bushy plant habit; vigorous growth habit.

*Plant height.*—About 13 cm.

*Plant width.*—About 60 cm.

*Lateral branch description.*—Length: About 36 cm. Diameter: About 1.7 mm. Internode length: About 1.7 cm. Strength: Strong, flexible. Aspect: Outwardly spreading. Texture: Pubescent. Color: Close to 144A.

Leaf description:

*Arrangement.*—Alternate, simple; sessile.

*Length.*—About 4.3 cm.

*Width.*—About 1.8 cm.

*Shape.*—Elliptic to broadly lanceolate.

*Apex.*—Obtuse.

*Base.*—Cuneate.

*Margin.*—Shallowly crenate.

*Texture, upper surface.*—Slightly pubescent.

*Texture, lower surface.*—Pubescent.

*Venation pattern.*—Pinnate.

*Color.*—Developing and fully expanded leaves, upper surface: Close to 144A; venation, close to 144C. Developing and fully expanded leaves, lower surface: Close to 144B; venation, close to 144D.

Flower description:

*Flower arrangement, habit and shape.*—Flowers typically arranged in terminal and lateral racemes; flowers face mostly outwardly to slanting downward; freely flowering habit with about eight flowers per inflorescence and about 280 flowers developing per plant; flowers bilabiate with two upper petals and three larger lower petals.

*Fragrance.*—None detected.

*Natural flowering season.*—In Japan, plants of the new Lobelia flower continuously from May until October; early flowering habit, plants begin flowering about three to four weeks after planting.

*Flower longevity on the plant.*—Longevity of individual flowers is highly dependent on temperature, flowers typically last about 10 to 14 days on the plant; flowers persistent.

*Inflorescence length.*—About 11.2 cm.

*Inflorescence diameter.*—About 8.3 cm.

*Flower length.*—About 2.1 cm.

*Flower diameter.*—About 2.5 cm.

*Flower tube length.*—About 9 mm.

*Flower tube diameter.*—About 5.3 mm.

*Flower buds.*—Length: About 1.4 cm. Diameter: About 5.1 mm. Shape: Club-shaped. Color: Close to 145C.

*Petals.*—Arrangement: Single whorl of five petals fused towards the base; two upper petals and three larger lower petals. Upper petals: Length, beyond throat: About 9 mm. Width: About 3.2 mm. Shape: Spatulate. Apex: Acute. Margin: Entire. Texture, upper and lower surfaces: Smooth, glabrous. Lower petals: Length, beyond throat: About 9.7 mm. Width: About 9.5 mm. Shape: Ovate. Apex: Obtuse. Margin: Entire. Texture, upper and lower surfaces: Smooth, glabrous. Color, upper petals: When opening, upper and lower surfaces: Close to NN155C. Fully opened, upper and lower surfaces: Close to NN155C; color does not change with development. Color, lower petals: When opening, upper and lower surfaces: Close to NN155C. Fully opened, upper and lower surfaces: Close to NN155C; color does not change with development. Color, throat, upper and lower petals: Close to NN155C; nectar guides, close to 144C. Color, tube, upper and lower petals: Close to NN155C.

*Sepals.*—Arrangement: Single whorl of five sepals, fused at the base; star-shaped calyx. Length: About 6.9 mm. Width: About 1.2 mm. Shape: Lanceolate. Apex: Acute. Margin: Entire. Texture, upper and lower surfaces: Smooth, glabrous. Color: When opening and fully opened, upper surface: Close to 137B. When opening and fully opened, lower surface: Close to 137C.

*Pedicels.*—Length: About 2.8 cm. Diameter: About 0.5 mm. Strength: Strong, flexible. Texture: Smooth, glabrous. Color: Close to 137B.

*Reproductive organs.*—Stamens: Quantity per flower: Five. Stamen length: About 6.8 mm. Anther size: About 1.1 mm by 2.7 mm. Anther shape: Elliptic. Anther color: Close to N199C. Pollen amount: Moderate. Pollen color: Close to 4D. Pistils: Quantity per flower: One. Pistil length: About 9.4 mm. Stigma shape: Bi-lobate. Stigma color: Close to 85C. Style color: Close to 144C. Ovary color: Close to 144A.

*Fruits and seeds.*—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 28° C.

It is claimed:

1. A new and distinct *Lobelia* plant named 'Sunlobe Toreho' as illustrated and described.

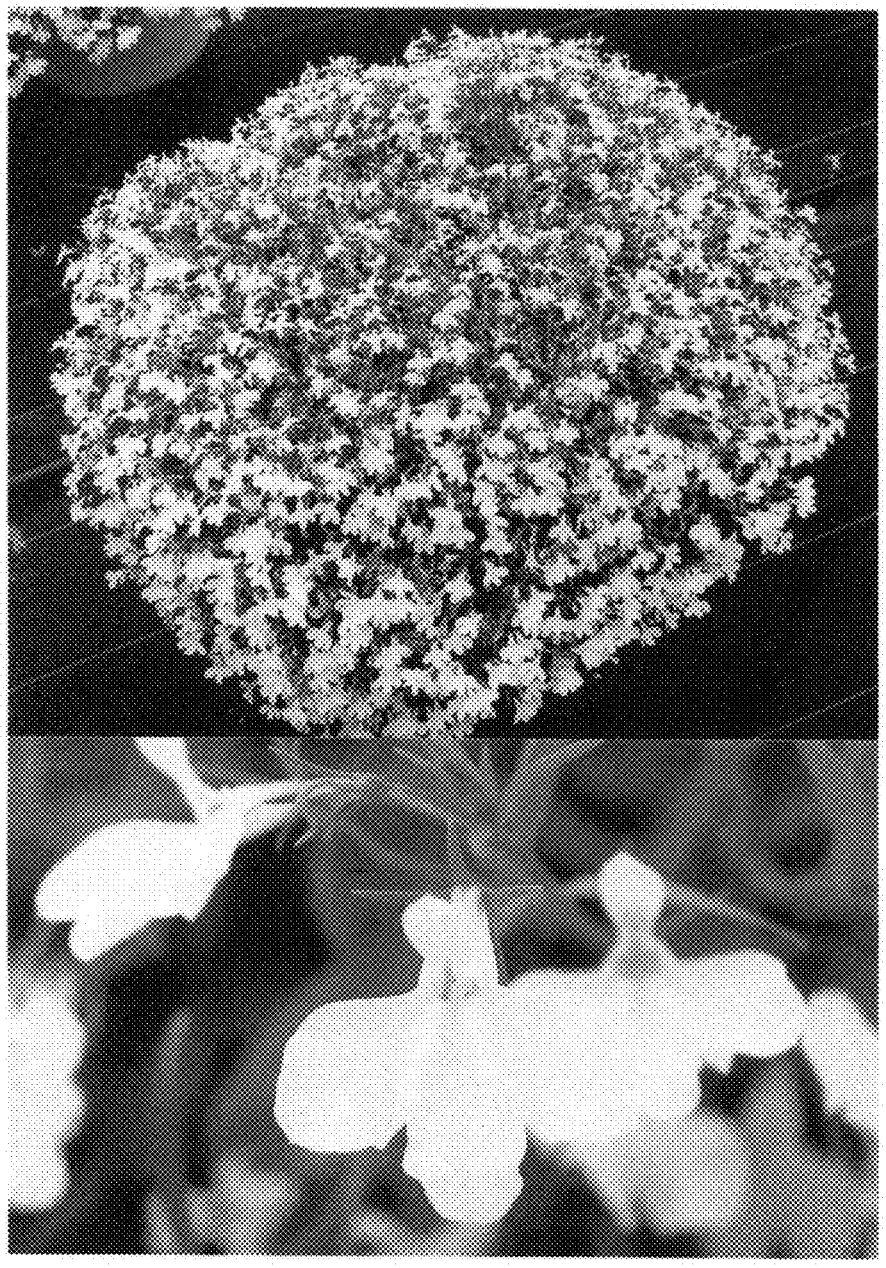

* * * * *